(12) United States Patent
Edidin et al.

(10) Patent No.: US 8,702,594 B2
(45) Date of Patent: Apr. 22, 2014

(54) IMAGING SYSTEM HAVING A QUICK CONNECT COUPLING INTERFACE

(76) Inventors: Avram Allan Edidin, Portola Valley, CA (US); Xiaolong Ouyang, Palo Alto, CA (US)

( * ) Notice: Subject to any disclaimer, the term of this patent is extended or adjusted under 35 U.S.C. 154(b) by 0 days.

(21) Appl. No.: 13/276,839

(22) Filed: Oct. 19, 2011

(65) Prior Publication Data
US 2012/0100729 A1 Apr. 26, 2012

Related U.S. Application Data

(60) Provisional application No. 61/405,420, filed on Oct. 21, 2010, provisional application No. 61/418,236, filed on Nov. 30, 2010.

(51) Int. Cl.
*A61B 1/00* (2006.01)
*H01R 13/62* (2006.01)

(52) U.S. Cl.
USPC ........... 600/136; 600/132; 600/146; 600/151; 439/38; 439/39; 439/40

(58) Field of Classification Search
USPC ............. 600/136, 139, 146, 149, 132, 109; 439/38–40
See application file for complete search history.

(56) References Cited

U.S. PATENT DOCUMENTS

| | | | |
|---|---|---|---|
| 5,329,936 A * | 7/1994 | Lafferty et al. | 600/109 |
| 5,667,476 A * | 9/1997 | Frassica et al. | 600/149 |
| 6,059,719 A * | 5/2000 | Yamamoto et al. | 600/127 |
| 6,221,070 B1 * | 4/2001 | Tu et al. | 606/41 |
| 7,507,205 B2 * | 3/2009 | Borovsky et al. | 600/466 |
| 7,780,650 B2 * | 8/2010 | Frassica et al. | 604/544 |
| 8,052,609 B2 * | 11/2011 | Harhen | 600/462 |
| 2003/0023142 A1 * | 1/2003 | Grabover et al. | 600/143 |
| 2004/0054259 A1 * | 3/2004 | Hasegawa et al. | 600/152 |
| 2006/0287576 A1 * | 12/2006 | Tsuji et al. | 600/132 |
| 2007/0060789 A1 * | 3/2007 | Uchimura et al. | 600/110 |
| 2007/0129604 A1 * | 6/2007 | Hatcher et al. | 600/136 |
| 2007/0173693 A1 * | 7/2007 | Refael | 600/144 |
| 2007/0225556 A1 * | 9/2007 | Ortiz et al. | 600/109 |
| 2007/0238927 A1 * | 10/2007 | Ueno et al. | 600/145 |
| 2008/0234547 A1 * | 9/2008 | Irion et al. | 600/133 |
| 2008/0262306 A1 * | 10/2008 | Kawai | 600/118 |
| 2008/0300456 A1 * | 12/2008 | Irion et al. | 600/109 |
| 2009/0149713 A1 * | 6/2009 | Niida | 600/167 |
| 2010/0191051 A1 * | 7/2010 | Miyake et al. | 600/104 |
| 2010/0234736 A1 * | 9/2010 | Corl | 600/463 |
| 2011/0034769 A1 * | 2/2011 | Adair et al. | 600/110 |
| 2011/0105839 A1 * | 5/2011 | Hoffman et al. | 600/104 |

(Continued)

*Primary Examiner* — John P Leubecker
*Assistant Examiner* — Arnaldo Torres Diaz
(74) *Attorney, Agent, or Firm* — Maschoff Brennan

(57) ABSTRACT

An imaging system can include a base unit and one or more imaging units. The base unit can include a main interface that has a plurality of main electrical connectors and one or more main mechanical connectors. A mechanical system is located in the base unit. Each imaging unit can include an elongate support member having a proximal end, a proximal section, a bendable section, and a distal end. Also, an imaging interface that couples with the main interface can be included on the proximal end of the elongate support member. The imaging interface includes a plurality of imaging electrical connectors that correspond and connect with the main electrical connectors of the main interface and includes one or more imaging mechanical connectors that correspond and connect with main mechanical connectors of the main interface. Mechanical actuators can bend the bendable section under control from the base unit.

19 Claims, 9 Drawing Sheets

(56) References Cited

U.S. PATENT DOCUMENTS

2011/0130627 A1* 6/2011 McGrail et al. ............... 600/109
2011/0213206 A1* 9/2011 Boutillette et al. ........... 600/146
2012/0016191 A1* 1/2012 Ito et al. ........................ 600/104
2012/0226103 A1* 9/2012 Gunday et al. ................ 600/118
2012/0245418 A1* 9/2012 Boulais ......................... 600/142

* cited by examiner

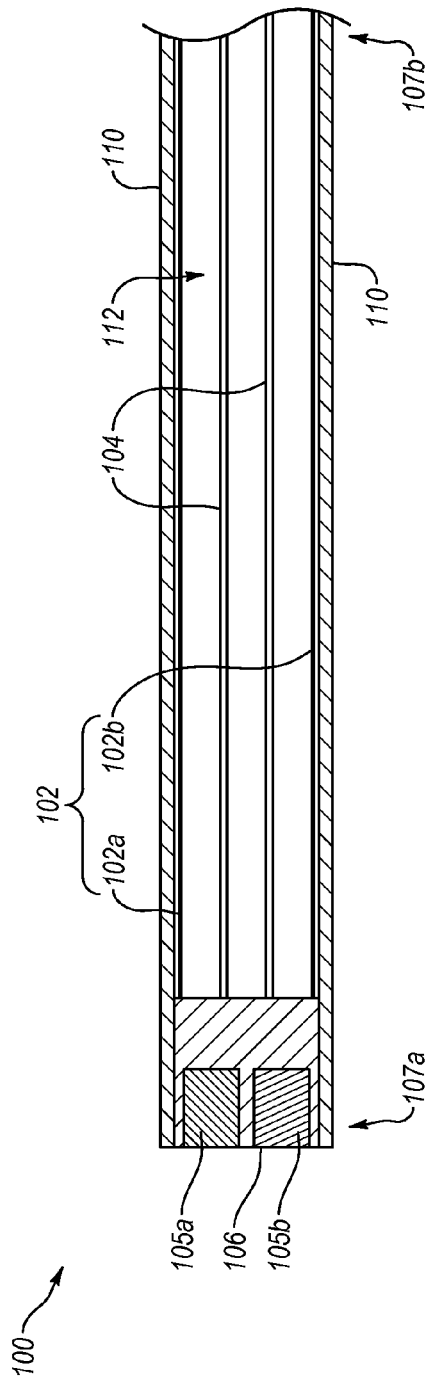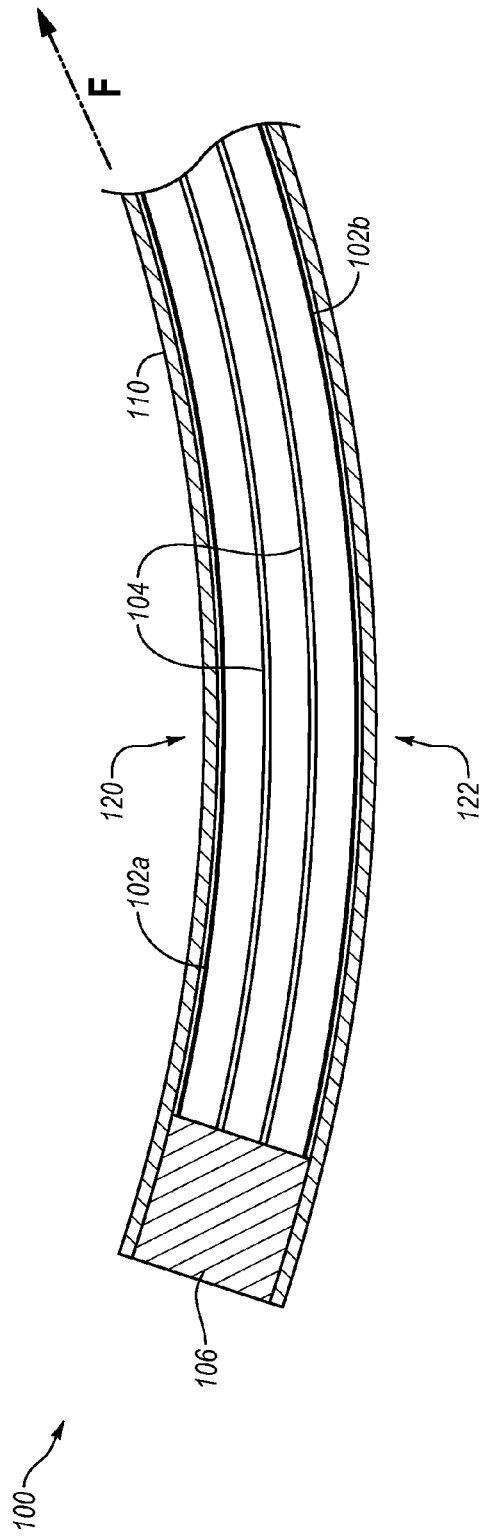

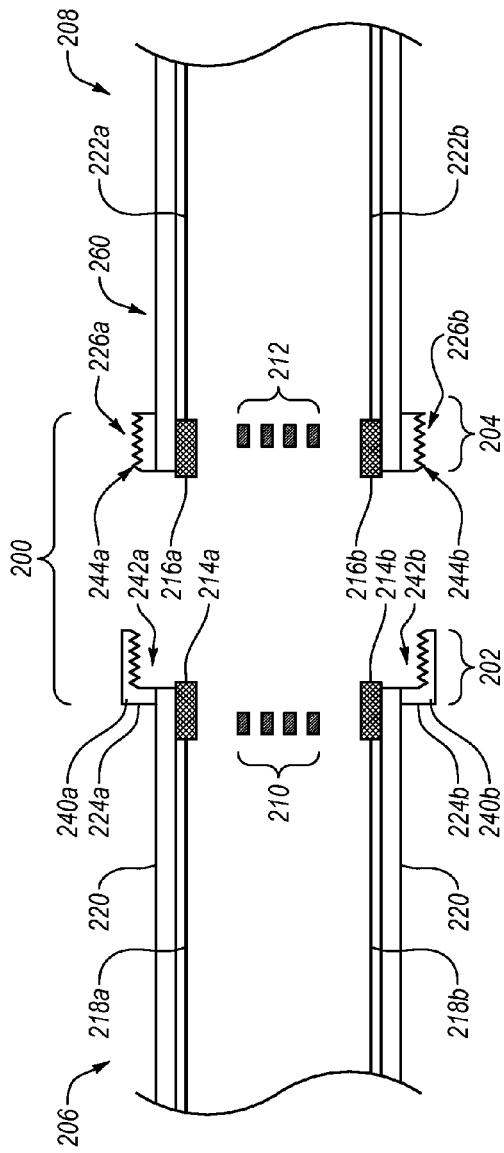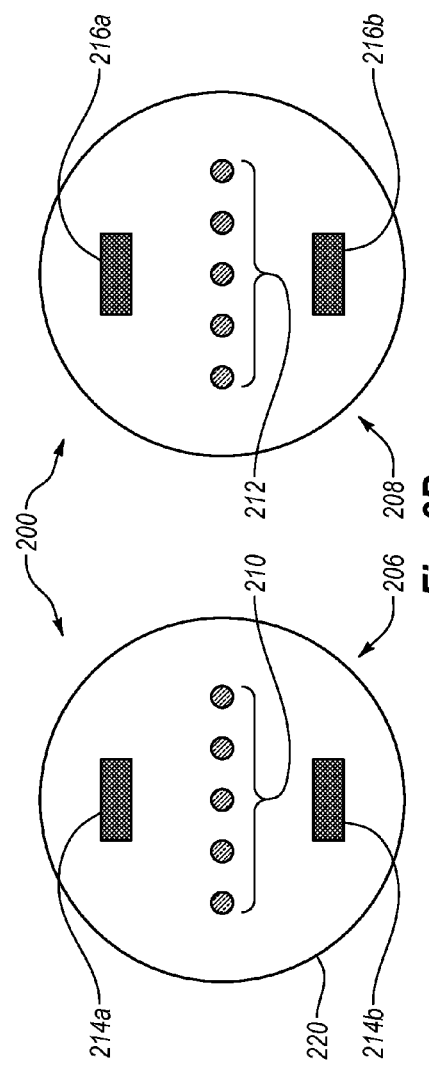

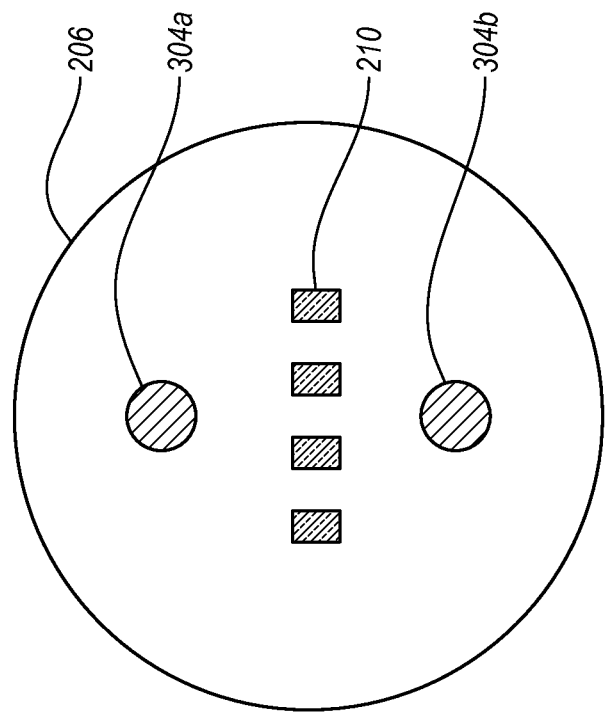
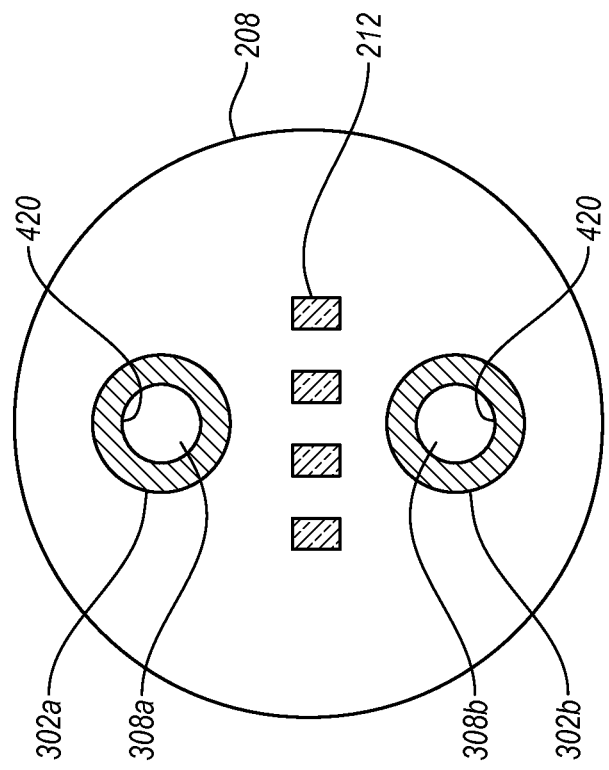
Fig. 4B

IMAGING SYSTEM HAVING A QUICK
CONNECT COUPLING INTERFACE

CROSS-REFERENCE TO RELATED
APPLICATIONS

This patent application claims the benefit of U.S. Provisional Patent Application No. 61/405,420, filed Oct. 21, 2010 and U.S. Provisional Patent Application No. 61/418,236, filed Nov. 30, 2010, which provisional patent applications are both incorporated herein by specific reference in their entirety.

BACKGROUND

Sensors and manipulators for surgical procedures, such as may be implemented as endoscopic devices, may be mechanically and/or electrically operated. Increasingly, focus in the healthcare industry is on minimally invasive and in-office medical diagnoses and procedures. In connection with minimally invasive and in-office medical diagnoses and procedures, it may be desirable to have disposable sensors and manipulators which mate with a non-disposable or reusable base unit. The base unit may be and/or may include a computer, a sample collector, a handheld display unit, or any other base unit to which a sensor or manipulator is attached.

For reasons of convenience, traceability, and sterility it may be advantageous for the sensors and manipulators to be disposable. A means of reliably and efficiently connecting disposable units to a corresponding reusable base unit may be useful in this context.

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1A includes a schematic representation of an embodiment of an imaging unit in a straight orientation;

FIG. 1B includes a schematic representation of an embodiment of the imaging unit of FIG. 1A in a bent or malleable orientation;

FIG. 2A includes a schematic representation of an embodiment of an interface between a base unit and an imaging unit;

FIG. 2B includes schematic representation of an end view of the interface of FIG. 2A;

FIG. 4B includes a schematic representation of an end view of the interface of FIG. 4A;

DETAILED DESCRIPTION

Figure 1C:
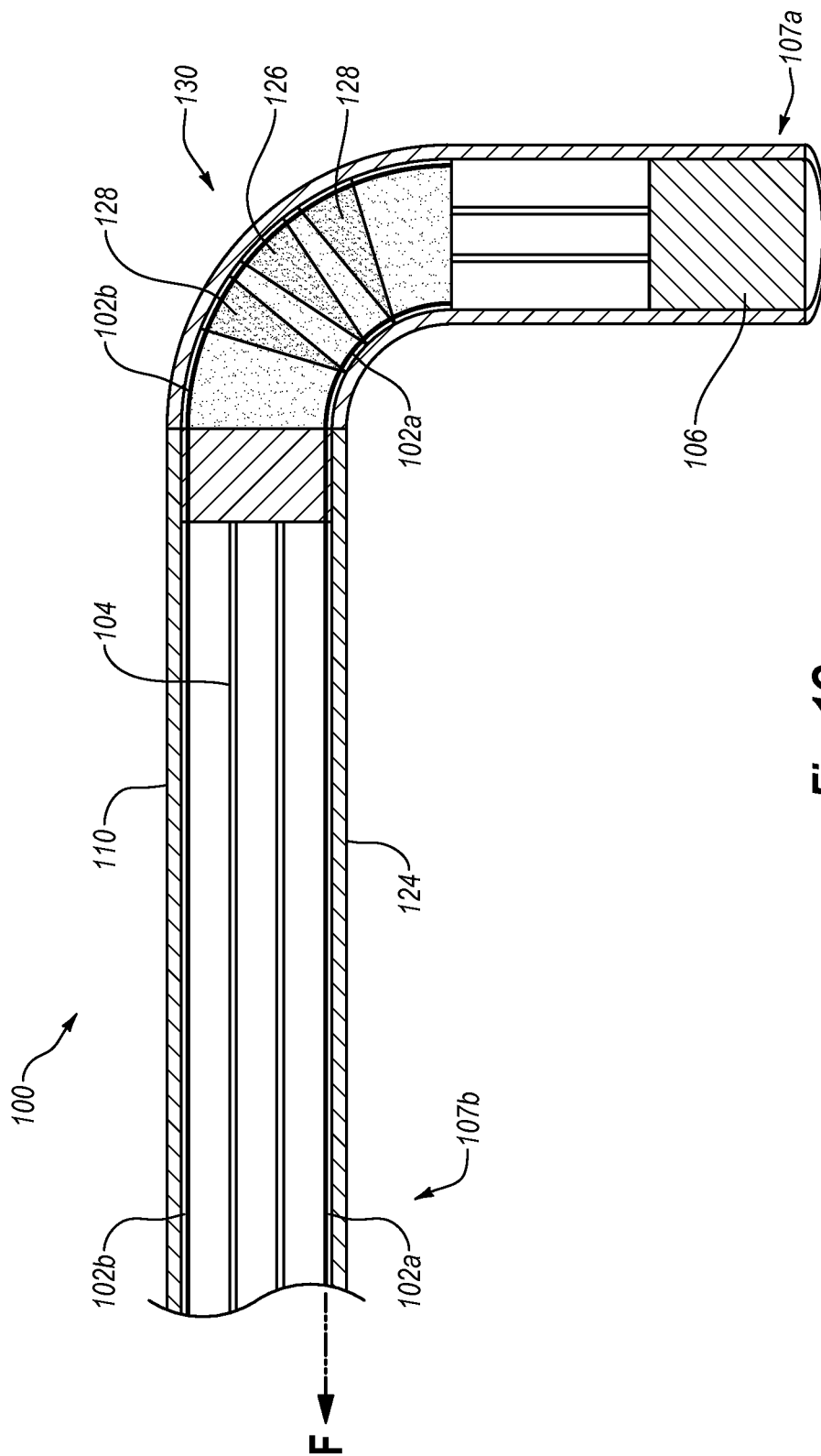
FIG. 1C includes a schematic representation of an embodiment of the imaging unit of FIG. 1A in a bent or malleable orientation at about 90 degrees or more.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to an imaging system that includes a reusable base unit and one or more imaging units. The imaging units can be disposable. For reasons of convenience, traceability, and sterility it may be advantageous for the sensors and manipulators to be disposable. A means of reliably and efficiently connecting disposable units to a corresponding reusable base unit may be useful in this context. The imaging system can be adapted to image internal organs or other tissues of a subject, such as a human. The imaging system may also be used to image internal areas of complex mechanical systems.

The imaging medical device of the present invention may be configured as a disposable imaging unit that couples to a reusable base unit. The disposable imaging unit may have one or more mechanical elements and one or more electrical elements unified into a single assembly. For instance, the disposable imaging unit can include a disposable imaging module constructed so as to permit distal articulation of a camera and light source. As such, the disposable imaging unit may include both mechanical elements and electrical elements.

In these and other embodiments, power to the camera and light source and mechanical, magnetic or electromagnetic force(s) may both be coupled across an interface between the disposable imaging unit and a corresponding non-disposable or reusable base unit. The ability to transfer power and mechanical forces allows for the disposable imaging unit to have the functionality of imaging and mechanical manipulation once the disposable imaging unit is coupled to the reusable base unit. As such, the interface can provide an electronic connection system that includes a first electronic connection interface on the disposable imaging unit side and a second electronic connection interface on the reusable base unit side. The electronic connection system allows for electronic signals as well as power to be passed from the reusable base unit to the disposable imaging unit and vice versa. The interface can also include a mechanical connection system that includes a first mechanical connection interface on the disposable imaging unit side and a second mechanical connection interface on the reusable base unit side, which first and second mechanical connection interfaces connect in order for mechanical forces, tension, compression, or other bias to be transferred from the reusable base unit side to the disposable imaging unit. The disposable imaging unit can then perform mechanical manipulations via forces generated and/or propagated by the reusable base unit. The mechanical connection system facilitates transfer of forces, tension, compression, or other bias or mechanical manipulation to the disposable imaging unit for mechanical functionality.

The reusable base unit can be any standard medical base unit that has electronic and mechanical modules to provide electronic data and mechanical manipulation to the imaging unit. The imaging unit can include a support member, mechanical actuator, electrically conductive elements, one or more imaging modules, one or more mechanical components, and an electronic/mechanical interface. The support member can be any type of support member common medical devices that be used percutaneously or within some body cavity or lumen, such as a catheter-type support member. The mechanical actuator can be located in the support member and can extend from a distal end to a proximal end of the support member. The electrically conductive elements can be located within the support member and configured for providing electrical power to one or more electrical elements, such as imaging and/or lighting modules located in the support member. The imaging modules can be configured to record images as well as illuminate the subject to be recorded. The mechanical components can be configured to articulate the end of the support member and/or provide some mechanical function that may or may not be therapeutic or medical in nature. The electronic/mechanical interface can be at the proximal end of the support member, and can be configured to receive data, electrical power, and mechanical forces from the reusable base unit. The electronic/mechanical interface can also be configured to be removably coupled with the reusable base unit through a corresponding and compatible interface on the reusable base unit.

The electronic/mechanical interface can include a force transfer contact member and a plurality of electrical contacts. The force transfer contact member can be coupled to the mechanical actuator and configured to transfer mechanical forces from the base unit to the mechanical actuator. That is, mechanical forces on the reusable base unit side are transferred to the mechanical actuator across the force transfer contact member. The plurality of electrical contacts can be coupled to the electrically conductive elements in the support member and configured to transfer electrical power and electronic data from the base unit to the plurality of electrically conductive elements. One or more of the plurality of electrical contacts can be configured to transfer electronic data from the disposable unit to the base unit.

The force transfer contact member can be configured in various ways in order for a force to transferred thereacross such that the mechanical actuator can be actuated from the base unit. The force transfer contact member can include any type of fastener that fastens the mechanical actuator to a mechanical controller in the base unit. The fastener can be any type of that allows coupling with force to be transferred thereof, which can include a nut and bolt, hook and eyelet, snap coupling, magnet or adhesive. In one example, the force transfer contact member can include a permanent magnet member, ferromagnetic member, or electromagnet member with the base unit side having a corresponding force transfer contact member. When the force transfer contact member includes an adhesive, any adhesive material suitable for the materials of the actuator member and other components can be used, where cyanoacrylates, epoxies, silicones, or the like can be used.

The electronic/mechanical interface can include one or more engagement features that are configured to removably engage corresponding engagement features of the base unit. The engagement features of the base unit and disposable imaging unit, when coupled together, prevent inadvertent decoupling of the disposable imaging unit from the base unit.

The disposable imaging unit can have various configurations, such as those illustrated and described herein, were features of one figure and description can be combined with any other features of any other figure or embodiment, FIG. 1A illustrates a disposable imaging unit 100 including both mechanical elements 102 and electrical elements 104. The mechanical elements 102 can include one or more mechanical actuators as described herein. The disposable imaging unit 100 can include a disposable imaging module 106 that has a camera module 105a and light source 105b. The imaging module 106 is located at a distal end 107a of the disposable imaging unit that is opposite of a proximal end 107b as in the illustrated embodiment of FIG. 1A. As depicted in FIG. 1A, the mechanical elements 102 include two thin wires 102A, 102B or other mechanical actuators running along a support member 110 of the disposable unit 100. Here, the support member 110 includes a tubular body having an internal lumen 112 that contains the mechanical elements 102 and electrical elements 104.

The support member 110 may be made of a flexible material, for instance. Such a configuration may enable articulation of the disposable unit 100 to bend in one or more planes. In particular, by applying sufficient tension in an appropriate direction to one of the mechanical elements 102 (e.g., wire 102A), a length of the mechanical element 102A can be drawn to the base unit so as to effectively shorten one side 120 of the support member 110 compared to the other side 122 so as to cause a curvature to be created in the support member, as generally illustrated in FIG. 1B. The arrow shows the mechanical element 102A being pulled proximally or toward the base unit.

In more detail, FIG. 1C depicts a disposable unit 100 having a support member 120 including a sheath 124 and a bending section 126 that bends when tension (shown by arrow) is applied to one of the mechanical elements 102a. The bending section 126 can be uniform or segmented with segments 128 as shown. The bending section 126 can have a bendable sleeve 130 covering the segments 128. The bending section 126 allows for the distal end 107a to bend. The bending section 126 can be configured to bend in the two planes or in any direction by articulation of one or more mechanical elements 102. Two mechanical elements 102 can cooperate to bend the distal end 107a in the plane of the figure page as shown. Two other or orthogonally oriented mechanical elements 102 can cooperate to bend the distal end 107a in the plane that bisects or is normal to the plane of the figure page. The use of two mechanical elements 102 for each bending plane allows for bending in both directions, such as the direction shown which appears down, an upward direction opposite as shown, or into or out from the page as well as in any direction of bending therebetween in a combination of the planes.

In these and other embodiments, an electrical interface (not shown) may be provided to transfer electrical power to the camera module 105a and light source 105b in the disposable imaging unit 100 from a corresponding base unit in any suitable manner. The electrical interface can be any specific electrical interface or any suitable type of electrical interface now known or later developed.

Additionally, a mechanical transfer interface (not shown) may be provided that permits the disposable unit 100 to be removably attached to a corresponding base unit, and transfers force(s) between the base unit and the disposable imaging unit 100 for operating the mechanical elements 102 of the disposable unit 100. Accordingly, some embodiments disclosed herein provide a connectable-detachable interface that transfers both mechanical force and electrical power through the same connector.

One example of a connectable detachable interface 200 according to some embodiments is illustrated in FIGS. 2A and 2B, which respectively illustrate a functional diagram (FIG. 2A) and an end view (FIG. 2B) of the connectable detachable interface 200. In the illustrated embodiment of FIGS. 2A-2B, aspects of the connectable detachable interface 200 are separated into a disposable unit interface 202 and a base unit interface 204 of a respective disposable unit 206 and base unit 208.

The connectable detachable interface 200 includes first electrical contacts 210 in the disposable unit interface 202 and second electrical contacts 212 in the base unit interface 204. Although not shown, first electrical contacts 210 of the disposable unit interface 202 may each be coupled to a corresponding trace, wire, or other electrically conductive element (e.g., shown in FIGS. 1A-1C) within the disposable unit 206 for carrying electrical power or data from or to the first electrical contacts 210. Analogously, the second electrical contacts 212 of base unit interface 204 may each be coupled to a corresponding trace, wire, or other electrically conductive element within the base unit 208 for carrying electrical power or data to or from the second electrical contacts 212. The first electrical contacts 210 and second electrical contacts 212 couple in order for power and data to be provided from the base unit 208 to the disposable unit 206, or vice versa. Accordingly, the first and second electrical contacts 210, 212 are configured such that after the disposable unit 206 is removably coupled to the base unit 208, each of first electrical contacts 210 is in contact with a corresponding one of the second electrical contacts 212. Thus, electrical power and/or data can be transferred to/from the disposable unit 206 from/to the base unit 208 via the electrical contacts 210, 212 provided in the connectable detachable interface 200.

The connectable detachable interface 200 further includes one or more first force transfer contacts 214a, 214b in the disposable unit interface 202 and one or more second force transfer contacts 216a, 216b in the base unit interface 204. Each first force transfer contact 214a, 214b of the disposable unit interface 202 can be coupled to a respective wire 218a, 218b or other mechanical actuator within the support member 220 of the disposable unit 206. The wires 218a, 218b may correspond to the mechanical elements 102a, 102b of FIGS. 1A-1C. Analogously, each second force transfer contact 216a, 216b of the base unit interface 204 can be coupled to a respective wire 222a, 222b or other mechanical element of the base unit 208.

The first force transfer contacts 214a, 214b and second force transfer contacts 216a, 216b are configured such that after the disposable unit 206 is removably coupled to the base unit 208, the first force transfer contacts 214a, 214b of disposable unit interface 202 are respectively coupled to the second force transfer contacts 216a, 216b of base unit interface 204. Moreover, the first force transfer contacts 214a, 214b of disposable unit interface 202 may be respectively coupled to the second force transfer contacts 216a, 216b of the base unit interface 204 such that some or all of the forces applied to the second force transfer contacts 216a, 216b of base unit interface 204 by mechanical elements 222a, 222b in base unit 208 may be transferred to the first force transfer contacts 218a, 218b in disposable unit 206 through the second force transfer contacts 214a, 214b of the disposable unit interface 202. Thus, actuation of the mechanical elements 222a, 222b of the base unit 208 can actuate the mechanical elements 218a, 218b of the disposable unit 206.

Each of the force transfer contacts 214a, 214b, 216a, 216b may include any suitable configuration to permit forces to be transferred through the connectable detachable interface 200. In some embodiments, for example, each of the force transfer contacts 214a, 214b, 216a, 216b can be a permanent magnet, with the magnetic poles of force transfer contacts 214a, 214b, 216a, 216b being appropriately oriented such that the corresponding force transfer contacts 214a, 216a are attracted to each other and the corresponding force transfer contacts 214b, 216b are also attracted to each other when the disposable unit 206 is removably coupled to the base unit 208.

Alternately, one or both of the first force transfer contacts 214a, 214b of disposable unit interface 202 may be a permanent magnet while one or both of the second force transfer contacts 216a, 216b in base unit interface 204 may be a ferromagnetic material. Alternately or additionally, one or both of the first force transfer contacts 216a, 216b in base unit interface 204 may be a permanent magnet while one or both of the second force transfer contacts 214a, 214b in disposable unit interface 202 may be a ferromagnetic material.

In one embodiment, one or both of the first force transfer contacts 214a, 214b in the disposable unit interface 202 may be an electromagnet, while one or both of second force transfer contacts 216a, 216b in base unit interface 204 may be a ferromagnetic material. Alternately or additionally, one or both of the second force transfer contacts 216a, 216b in the base unit interface 204 may be an electromagnet, while one or both of the first force transfer contacts 214a, 214b in the disposable unit interface 202 may be a ferromagnetic material. The first and second force transfer contacts can be mixed with a combination of multiple types on the disposable unit 206 and a combination of multiple types on the base unit 208.

In one embodiment, an adhesive may be pre-applied to the first force transfer contacts 214a, 214b of the disposable unit interface 202 or to the second force transfer contacts 216a, 216b of the base unit interface 204, which would be exposed prior to attachment of the disposable unit 206 to the base unit 208.

The specific configurations of the first and second force transfer contacts 214a, 214b, 216a, 216b disclosed herein are provided by way of example only and not limitation. Further, the specific configurations of first and second force transfer contacts 214a, 214b, 216a, 216b disclosed herein are not mutually exclusive and can be combined or modified as desired.

Alternately or additionally, the connectable detachable interface 200 may further include one or more first engagement features 224a, 224b (FIG. 2A) in the disposable unit interface 202 and one or more second engagement features 226a, 226b (FIG. 2A) in the base unit interface 204. The first engagement features 224a, 224b are complementary to the second engagement features 226a, 226b, such that they are removably couplable together. As shown in FIG. 2A, the first engagement features 224a, 224b of disposable unit interface 202 may include one or more extensions 240a, 240b defining recesses 242a, 242b configured to receive the engagement features 226a, 226b of base unit interface 204, while the engagement features 226a, 226b of base unit interface 204 may include one or more protrusions 244a, 244b configured to be received within and engage the engagement features 224a, 224b of disposable unit interface 202. The recesses 242a, 242b may or may not include a surface that mates with the surface of the protrusions 244a, 244b. Of course, the positions of the extension/recess-type engagement features 224a, 224b and the protrusion-type engagement features 226a, 226b on disposable unit interface 202 and base unit interface 204 can be reversed. Alternately or additionally, other types of complementary engagement features can be implemented in the connectable detachable interface 200, which can include bolt and nut, hook and eyelet, or the like.

In some embodiments, the first engagement features 224a, 224b of disposable unit interface 202 are configured to be disengaged from the second engagement features 226a, 226b of base unit interface 204 by manipulating (e.g., squeezing) the distal end 260 of the base unit 208 or performing some other deliberate action. As such, the engagement features 224a, 224b, 226a, 226b may be configured to prevent inadvertent decoupling of the disposable unit 206 from the base unit 208.

The first and second force transfer contacts described herein that cooperate to transfer force from the base unit to the disposable unit can have various configurations. Passive configurations can include magnets or adhesives or other types of fasteners that are not electronically operably. However, active configurations can include electromagnets or other operable components that can be turned on or off with or without power.

Figure 3:
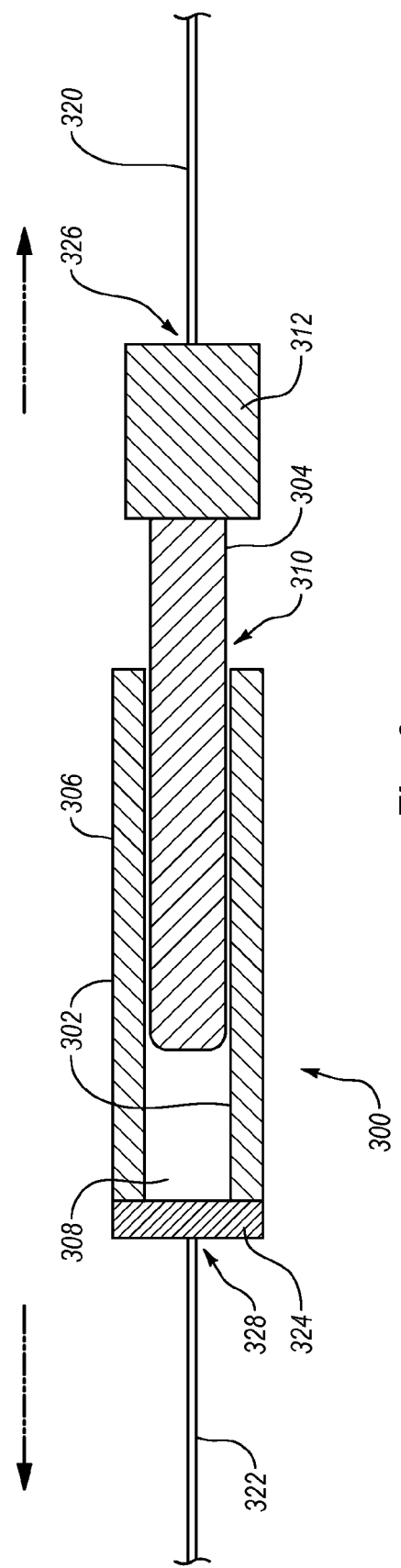
FIG. 3 includes a schematic representation of an embodiment of an electromagnetic mechanical coupling system.

With additional reference to FIG. 3, a force transfer contact system 300 can have a female force transfer contact 302 and a male force transfer contact 304 of the connectable detachable interface 200 illustrated in FIGS. 2A-2B. Either the male or female force transfer contact 302, 304 can be included in on the base unit or disposable unit. The female force transfer contact 302 may correspond to the second force transfer contacts 216a, 216b, while the male force transfer contact 304 may correspond to the first force transfer contacts 214a, 124b. In the example of FIG. 3, the female force transfer contact 302 includes an electromagnet 306 having a cavity 308 (e.g., a solenoid coil). The female force transfer contact 302 can define a cavity 308 configured to receive the male force transfer contact 304. As shown, the male force transfer contact 304 includes a ferromagnetic armature 310 configured to be received within and selectively moved (e.g., in an axial direction shown by the arrows) by the female force transfer contact 302 upon being turned on or turned off. When turned on, the male force transfer contact 304 can be received into and coupled with the female force transfer contact 302. When turned on, the male force transfer contact 304 can be removed or expelled from the cavity 308 of the female force transfer contact 302. The male force transfer contact 304 can include an enlarged section 312 that is too large to be received into the cavity 310.

FIG. 3 also shows that the female force transfer contact 302 can be coupled to a first mechanical element 322 through a first coupling 328 and the male force contact 304 can be coupled to a second mechanical element 320 through a second coupling 326. The female force transfer contact 302 can include a base member 324 that can facilitate the first coupling 328. These couplings can be any type of couplings as in known in the art to couple mechanical elements 320, 322 to functional members. These couplings can be brazings, welding, adhesive, knots, integration, or the like.

Figure 4A:
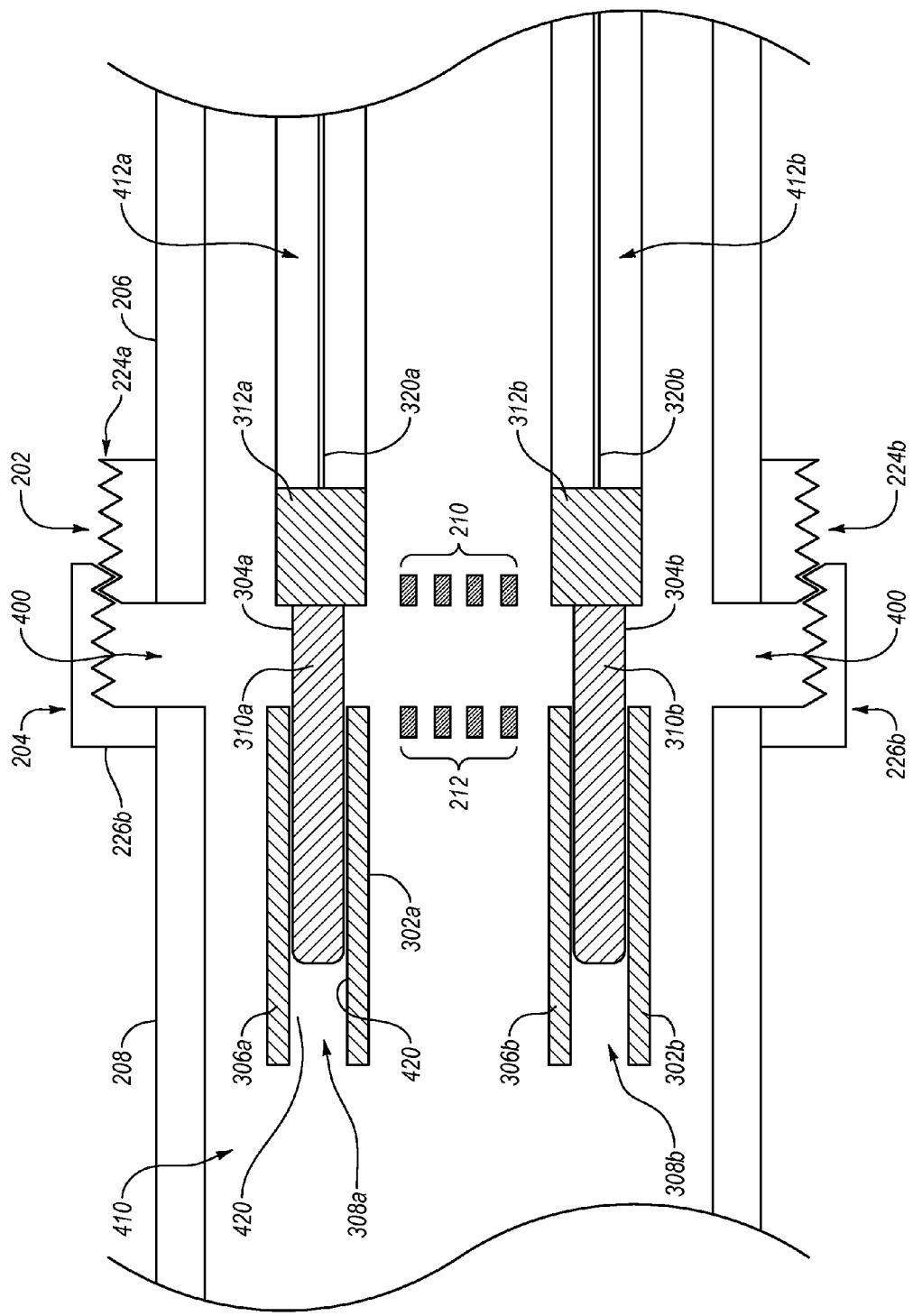
FIG. 4A includes a schematic representation of an embodiment of an interface between a base unit and an imaging unit of FIG. 2A having the electromagnetic mechanical coupling system of FIG. 3.

FIGS. 4A-4B illustrates an embodiment of a connectable detachable interface 400 including the force contact arrangement of FIG. 3 in the general configuration illustrated in FIGS. 2A-2B. FIG. 4A is similar to FIG. 2A, while FIG. 4B is similar to FIG. 2B. However, the connectable detachable interface 400 includes the female force transfer contact 302 in the base unit 208, while the male force transfer contact 304 is included in the disposable unit 206. Here, the base unit 208 includes a solid internal body 410 that encases the female force transfer contacts 302a, 302b so that they do not move relative thereto. The female force transfer contacts 302a, 302b include solenoids 306a, 306b, each having an internal cavity 308a, 308b. The internal cavities 308a, 308b each include an internal surface 420 that slidingly receives the male force transfer contacts 304a, 304b. On the other hand, the disposable unit 206 includes an internal lumen 412a, 412b for each of the mechanical elements 320a, 320b coupled to the male force transfer contacts 304a, 304b that allow the mechanical elements to slide with respect thereto. When the female force transfer contacts 302a, 302b are activated, the male force transfer contacts 302a, 302b are drawn into or further into the internal cavities 308a, 308b so as to actuate the mechanical elements 320a, 320b, and bend the bendable distal end in one direction or another.

In view of the figures, the disposable unit described herein can be configured to be coupled to a base unit. The disposable unit can include a support member to provide support to the device and components located therein, and may include the imaging and other modules as well as mechanical components to actuate bending of the distal end of the disposable unit. The disposable unit can also include a mechanical actuator extending along the support member from a proximal end that couples to the base unit to a distal end that includes a bendable section and a further distal imaging module. The disposable unit can include a plurality of electrically conductive elements disposed within the support member for providing electrical power to an electrical element, such as imaging module, of the disposable unit. The disposable unit can include a disposable unit interface configured to receive electrical power and mechanical forces from the base unit and to removably couple the disposable unit to the base unit. The base unit can include corresponding features, such as a housing, a mechanical actuator, electrically conductive elements, and a base unit interface that receives and mates with the disposable unit interface.

The disposable unit interface can include a force transfer contact coupled to the mechanical actuators located within the disposable unit. The force transfer contact can be configured to transfer mechanical forces from the base unit to the mechanical actuator. The disposable unit interface can include a plurality of electrical contacts coupled to the plurality of electrically conductive elements and configured to transfer electrical power from the base unit to the plurality of electrically conductive elements. The base unit interface can have a corresponding force transfer contact and corresponding plurality of electrical contacts.

The force transfer contacts of the disposable unit interface and base unit interface can be cooperatively configured. They can be adhesive or magnetic. When magnetic, they can include permanent magnets, ferromagnetic materials, or electromagnets.

The base unit and disposable unit interfaces may further include a plurality of corresponding engagement features configured to removably engage the base unit interface with the disposable unit interface. These corresponding engagement features can be adapted to prevent inadvertent decoupling of the disposable unit from the base unit.

Figure 5A:
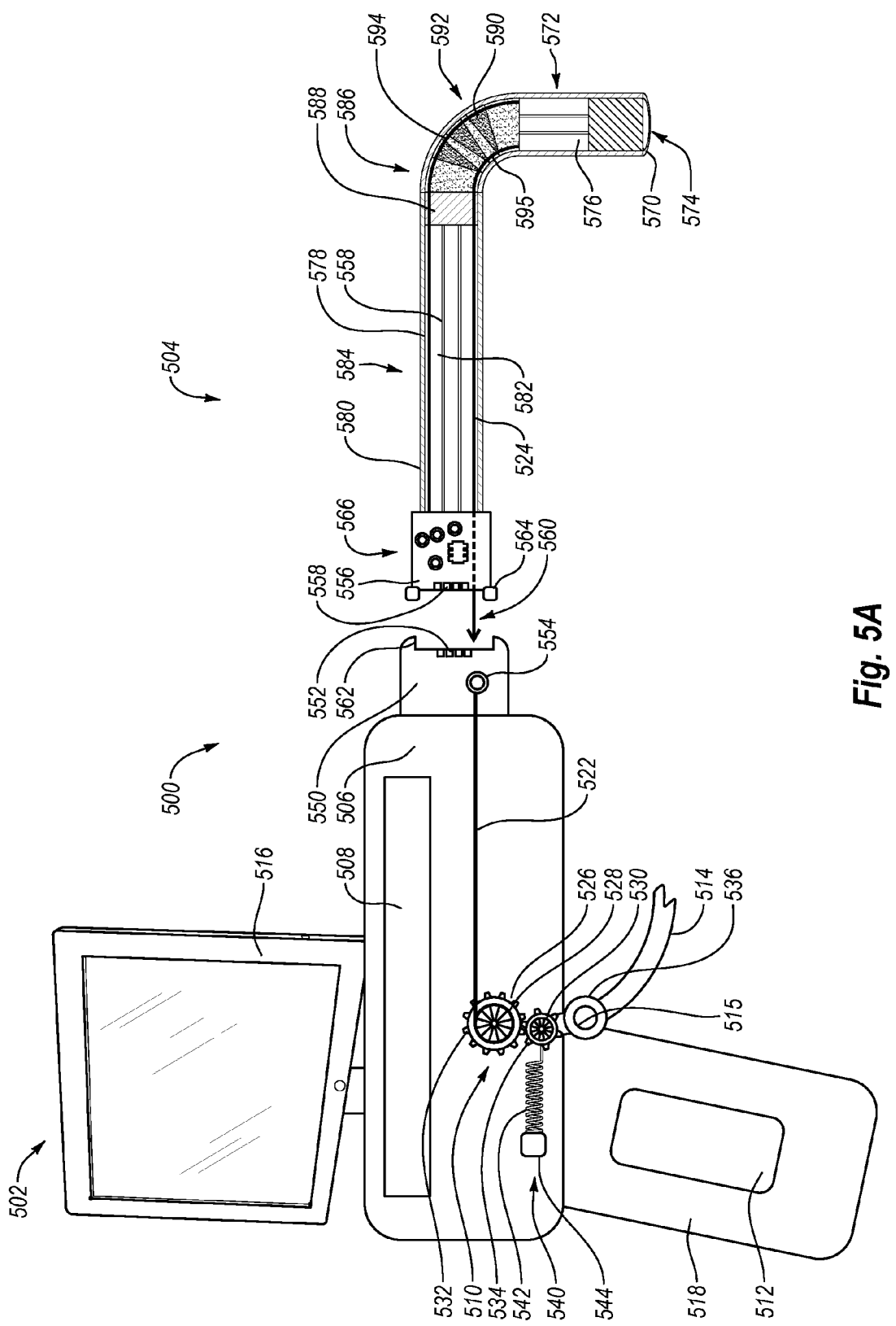
FIG. 5A includes a schematic representation of an embodiment of an imaging system having a base unit and an imaging unit.

FIG. 5A provides a schematic representation of a medical device 500. The medical device 500 can be configured with the components to function as a cytoscope, however, other components can be included for other functionalities. In the cytoscope configuration, the medical device 500 can include imaging modules.

The medical device 500 can include a reusable base unit 502 and a disposable imaging unit 504. The base unit 502 can include a main housing 506 that contains a system control module 508 which can control one or more electronic components of the base unit 502 and/or imaging unit 504. The main housing 506 can also include a mechanical system 510 that is coupled to a mechanical activating member 514 (e.g., activating lever) and mechanical deactivating member 515 (e.g., activating button). The main housing 506 may also include a power supply 512, which can be portable (e.g., batteries) or coupled with a wall power supply (e.g., cord to be plugged into wall outlet). The main housing 506 can include a gun shape with a handle 518 as illustrated or it may have some other shape configuration. The main housing 506 can also include a display screen 516 that can be integrated or couplable therewith. In one option, the disposable imaging unit 504 may be configured to be reusable and may have a disposable sheath (not shown).

The main housing 506 can include any type of mechanical system 510 that can transfer a force to a mechanical actuating member in order to bend the distal end of the disposable imaging unit 504. The mechanical system 510 functions to bend the distal end of the disposable imaging unit 504 in one or more planes, in either direction. As illustrated, one or more main force cables 522 can be included in the main housing 506 that can be functionally coupled to articulating force cables 524 of the disposable imaging unit 504, where activation of the articulating force cables 524 moves or bends the distal end of the disposable imaging unit 504.

The mechanical system 510 is illustrated to include a geared spindle 526, where one geared spindle 526 can be provided for each main force cable 522. In FIG. 5A, only one force cable 522 and geared spindle 526 are shown; however, there could be two per bending plane in embodiments capable of bending in both directions. A total of four force cables 522 and geared spindles 526 can allow for bending in both directions in both planes an in various bending orientations therebetween by using one or more of the geared spindles to apply tension to separate force cables. The geared spindle 526 can be activated by operating the mechanical activating member 514 in order to cause the geared spindle 526 to reel the force cable 522 so as to be wound around the geared spindle 526. The wound force cable 522 is represented by spooled force cable 528. The mechanical deactivating member 515 can be operated in order to release or let out the force cable 522 in order to reduce or remove tension and let the force cable relax so that the bendable section relaxes and straightens.

The main housing 506 can also include a main interface 550, which can be configured as described herein. The main interface 550 can have base electrical connectors 552 and one or more base mechanical connectors 554, which are on the base unit 502 side. The electrical connectors 552 can be operably coupled to the system control module 508, and the mechanical connectors 554 can be operably coupled to the mechanical system 510. The disposable imaging unit 504 can include an imaging interface 556 that has imaging electrical connectors 558 and one or more imaging mechanical connectors 560. The imaging electrical connectors 558 can correspond and electronically couple with the base electrical connectors 552. The imaging mechanical connectors 560 can be of the same number as and mechanically couple with the base mechanical connectors 554. The main interface 550 can have main engagement features 562 that mate with and receive imaging engagement features 564 of the imaging interface 556. The main interface 550 and imaging interface 556 can be configured as the interfaces of FIGS. 2A-2B and 4A-4B.

The imaging unit 504 can include a printed circuit board 566 (PCB 566) with some imaging components or other control modules. The PCB 566 can be configured to be one time programmable (OTP) as described in U.S. patent application Ser. No. 13/094,415, which is incorporated herein by specific reference in its entirety. The PCB 566 can be adjacent to the imaging interface 556, or distally associated with the imaging interface 556.

The PCB can be electronically coupled with electronic lines 568, which can be configured as electronic wires or other electronic paths capable of transmitting power and/or electronic data. The electronic lines 568 can extend along the length of the imaging unit 504 to a camera module 570 located at the distal end 572. The camera module 570 can be oriented to capture images from a distal opening 574 of the imaging unit 504. Optionally, the distal end 572 can include or be configured as a camera module housing 576 that houses the cameral module 570. The cameral module housing 576 can be of any suitable size; however, examples include having a length of about 2 to 20 mm, from 4 to 15 mm, or from 5 to 10 mm, and a width or diameter of about 2 mm to about 8 mm, from about 2.5 mm to about 5 mm, or from about 2.8 or 3 mm to about 4 mm The imaging interface 556 can be coupled with or otherwise associated with an elongate body 578 that is positioned between the imaging interface 556 and the distal end 572. The elongate body 578 can be similar to the support member described herein, and can be tubular in shape with one or more internal lumens 582, such as lumens for the articulating force cables 524 and/or for the electronic lines 558. The elongate body 578 can include a sheath 580, which can be individually disposable or the entire imaging unit 504 can be disposable. The sheath 580 can provide the outer surface of the imaging unit 504.

The elongate body 578 can have a proximal section 584, bendable section 586 and distal end section 572 (e.g., distal end 572) arranged in this order from proximal to distal. A joint coupling 588 can couple the proximal section 584 and bendable section 586. The joint coupling 588 can provide a joint to allow for the bending action. A sleeve or other coupling can be used as the joint coupling 588.

Figure 5B:
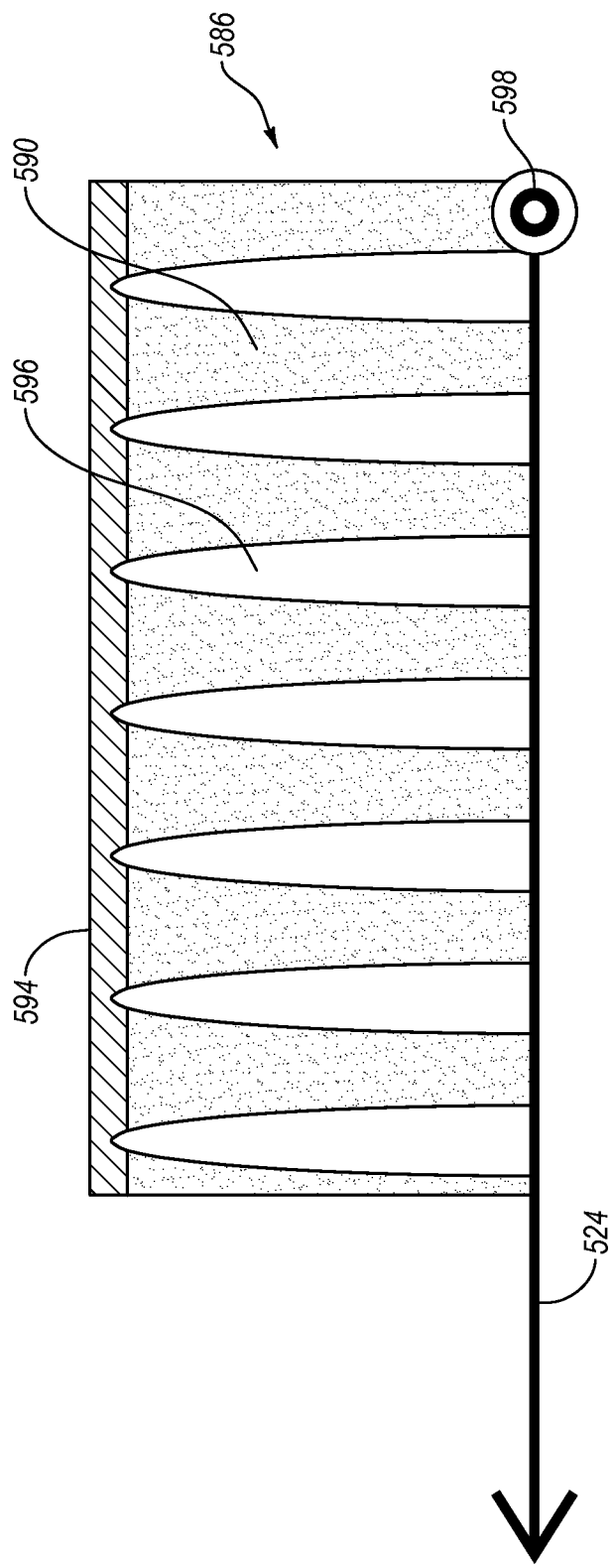
FIG. 5B includes a schematic representation of an embodiment of a bendable or malleable section of the imaging unit of FIG. 5A.

The bendable section 586 can have various configurations in order to bendable. Various types of bendable tubes can be adapted to use with the imaging unit 504. Here, the bendable section 586 is configured as shown in FIGS. 5A and 5B. The bendable section 586 can include one or more bendable segments 590, which can be configured for cooperating to bend in one or two directions in a plane. Various materials can be used to allow for the bending action and bending between the bendable segments 590. The bendable segments 590 can allow for a larger outside bending radius 592 and a smaller inner bending radius 595, where the smaller inner bending radius 595 is on the side of the bending direction that is opposite of the larger outside bending radius 592. The smaller inner bending radius 595 can range from 5 mm to 20 mm, from 6 mm to 15 mm, or from 7 mm to 10 mm In one embodiment, a shape memory member 594 can be included in the bendable section 586. In some instances, a plurality of shape memory members 594 can be used. The shape memory members 594 can be made of a shape memory allow, such as nitinol. When relaxed, the shape memory member 594 is straight. When the articulating force cables 524 is tensioned or pulled toward the base unit 502, the shape memory member 594 can bend to allow for the bendable section 586 to bend as desired. When tension or force is released from the articulating force cables 524, the shape memory member 594 can straighten the bendable section 586.

FIG. 5B shows an example of the bendable section 586, which includes the bendable segments 590 associated with the shape memory member 594. As illustrated, gaps 596 can be located between the bendable segments 590 to facilitate bending. Also, a coupling 598 can be used to couple a distal bendable segment 590 with the articulating force cable 524. When the articulating force cables 524 is pulled, the bending section 586 bends as shown in FIG. 5A. When the articulating force cables 524 is relaxed, the bending section 586 can straighten as shown in FIG. 5B.

Referring back to the mechanical system 510, the geared spindle 526 can be operably coupled with drive gear 530. The operably coupling can be by gear teeth 532 of the geared spindle 526 interlacing with gear teeth 534 of the drive gear 530. Accordingly, when the mechanical activating member 514 is activated, the drive gear 530 rotates in a first rotational direction so as to rotate the geared spindle 526 to reel in and wind the force cable 522 into spooled force cable 528. When the mechanical deactivating member 515 is activated, the drive gear 520 releases or rotates in a second rotational direction that is opposite of the first rotational direction so as to release or unwind the force cable 522 from the spooled force cable 528. The mechanical system 510 can include appropriate mechanical components in order to allow for these operations to be performed. For example, the mechanical activating member 514 and mechanical deactivating member 515 can both be operably coupled to a transfer component 536 that transfers the mechanical operations to the drive gear 530. Mechanical components and configuration for the mechanical system 510 can be designed in order to implement the functionality described herein.

In one embodiment, the drive gear 530 can be biased so that it rotates preferentially in one direction when unopposed by the gear spindle 536, mechanical activating member 514, and mechanical deactivating member 515. That is, the drive gear 530 can have a bias by having a bias system 540 operably coupled thereto. The bias system can include a bias element 542 (e.g., spring) coupled to the drive gear 530 in a manner that causes the drive gear 530 to preferentially rotate in one direction or the other. The bias element 542 can be coupled to an anchor 540 that is anchored to the main housing or some other intermediate component. Having one end anchored to the anchor 540 and the other end coupled to the drive gear 530 can apply a constant bias to the drive gear 530. The bias element 542 can cause the force cable 522 to be under tension or under slack depending on the design and orientation. In some instances it can be preferential for the force cable 522 to remain under tension, and in other instances it can be preferential for the force cable 522 to be slack until activated.

In one embodiment, the bias element 542 applies a bias to the drive gear 530 in a manner that applies tension to the force cable 522 through the spindle gear 526. As such, the bias pulls the force cable 522 so as to bend the distal end 572 of the imaging unit 504 if left without other acting forces or restraint. However, the mechanical activating member 514 acts on the drive gear 530 to hold it so that it does not rotate and thereby does not impart additional bias to the force cable 522. As desired, the mechanical activating member 514 can be activated in order to release the drive gear 530 that is biased by the bias element 542, which cases the drive gear 530 to rotate the spindle gear 526 in order to apply additional force or tension to the force cable 522. This function can take the bendable section 586 of the imaging unit 504 from straight to becoming bent or to a further bent position as shown in FIG. 5A. The mechanical deactivating member 515 can then be activated to release the tension or force from the force cable 522 so as to allow the bendable section 586 to become straightened as shown in FIG. 5B.

In one embodiment, the bias element 542 applies a bias to the drive gear 530 in a manner that releases tension to the force cable 522 through the spindle gear 526. As rest, there is no bias to pull the force cable 522 to bend the distal end 572 of the imaging unit 504 if left without other acting forces or restraint, and thereby the bendable section 586 is straight at rest. However, the mechanical activating member 514 can be activated to act on the drive gear 530 so that it rotates, and thereby imparts a bias or tension to the force cable 522. As desired, the mechanical activating member 514 can be activated in order to apply more force or tension to the force cable 522. The applied force to the force cable 522 can take the bendable section 586 of the disposable unit from straight to becoming bent or to a further bent position. The mechanical deactivating member 515 can then be activated to release the tension or force from the force cable 522 so as to allow the bendable section 586 to become straightened.

In one embodiment, the connection between the imaging unit and the base unit can be via magnetic interaction. The connection can include magnets on one side, either the base unit or imaging unit, and either oppositely poled magnets or magnetically responsive materials on the other unit. The connection members described herein can be the magnet and/or magnetically responsive material so long as there is a magnetic field that facilitates the connection between the base unit and imaging unit. In one example, the base unit can have stronger magnets and the imaging unit can have weaker magnets that are less expensive. The magnetic field can also be turned on or turned off when one or more electromagnets are used. These electromagnets can be on the base unit and/or the imaging unit. For example, the magnetic field can be turned on or off during coupling or decoupling of the base unit and imaging unit by turning on or turning off the electrical current to the electro magnet. In one example, the electromagnet can include an electromagnetic coil that can be selectively turned on to provide a magnetic field, and turned off to remove the magnetic field.

In one embodiment, an imaging system can include a base unit and one or more imaging units. The base unit can include: a housing; a system control module located in the housing; a main interface on the housing, the main interface includes a plurality of main electrical connectors operably coupled with the system control module and includes one or more main mechanical connectors; a mechanical system located in the housing and mechanically coupled with the one or more main mechanical connectors; and a mechanical activating member mechanically coupled with the mechanical system. The one or more imaging units can each be configured to be removably coupled to the base unit. Each imaging unit can include: an elongate support member having a proximal end, a proximal section, a bendable section, and a distal end; an imaging interface on the proximal end of the elongate support member, the imaging interface includes a plurality of imaging electrical connectors that correspond and connect with the main electrical connectors of the main interface and includes one or more imaging mechanical connectors that correspond and connect with main mechanical connectors of the main interface; one or more mechanical actuators each having a proximal end mechanically coupled with the one or more imaging mechanical connectors and extending from the imaging interface along the elongate support member to a distal region of the bendable section with is coupled to a distal end of the mechanical actuator; and a plurality of electrically conductive elements electronically coupled with the imaging electrical connectors and disposed within the elongate support member and extending from the imaging interface to an imaging module located in the distal end of the elongate support member.

In one embodiment, the main mechanical connectors and imaging mechanical connectors are configured as force transfer connectors when coupled. The force transfer connectors are configured to transfer mechanical forces from the mechanical system of the base unit to the one or more mechanical actuators in order to bend the bendable section of the elongate support member.

In one embodiment, the housing includes a power source that is operably coupled with one or more of the plurality of main electrical connectors, which are configured to transfer electrical power from the base unit to the imaging unit. The force transfer connectors can be adhesive or magnetic. When magnetic, the force transfer connectors include one or more of a permanent magnet, a ferromagnetic member, or an electromagnet.

In one embodiment, the base unit includes one or more main engagement members associated with the main interface and the imaging unit includes one or more imaging engagement members that are configured to be coupled with the one or more main engagement members when the base unit is coupled to the imaging unit.

In one embodiment, the one or more main engagement members are coupled with the one or more imaging engagement members when the base unit is coupled with the imaging unit.

In one embodiment, the bendable section of the elongate support member includes a shape memory member extending from a proximal end to a distal end of the bendable section. The shape memory member includes a shape memory alloy that is straight when in its relaxed state.

In one embodiment, the mechanical system includes a spindle gear coupled with a force cable at one end with the other end of the force cable being coupled with the one of the main mechanical connectors. Accordingly, activating the spindle gear winds the force cable therearound so as to apply a bias to the main mechanical connector. The mechanical system can include a drive gear engaged with the spindle gear and a mechanical activating member can be coupled with the drive gear such that activation of the mechanical activating member actuates the drive gear. In one aspect, the mechanical system can include a bias system coupled with the drive gear such that the bias system applies a bias to the drive gear.

In one embodiment, a disposable imaging unit can include: an elongate support member having a proximal end, a proximal section, a bendable section, and a distal end; an imaging interface located on the proximal end of the elongate support member, the imaging interface includes a plurality of imaging electrical connectors that correspond and connect with main electrical connectors of a main interface of a base unit, and the imaging interface includes one or more imaging mechanical connectors that correspond and connect with the main mechanical connectors of the main interface of the base unit; one or more mechanical actuators each having a proximal end mechanically coupled with the one or more imaging mechanical connectors and extending from the imaging interface along the elongate support member to a distal region of the bendable section with is coupled to a distal end of the mechanical actuator; and a plurality of electrically conductive elements electronically coupled with the imaging electrical connectors and disposed within the elongate support member and extending from the imaging interface to an imaging module located in the distal end of the elongate support member.

In one embodiment, the imaging mechanical connectors are configured as magnetic force transfer connectors when coupled to corresponding mechanical connectors of the base unit. The force transfer connectors are configured to transfer mechanical forces from the base unit to the one or more mechanical actuators in order to bend the bendable section of the elongate support member. The force transfer connectors can include one or more of a permanent magnet, a ferromagnetic member, or an electromagnet.

In one embodiment, the imaging interface includes one or more imaging engagement members that are configured to be coupled with one or more main engagement members when the base unit is coupled to the imaging unit.

In one embodiment, the bendable section of the elongate support member includes a shape memory member extending from a proximal end to a distal end of the bendable section. The shape memory member includes a shape memory alloy that is straight when in its relaxed state.

In one embodiment, a base unit can include: a housing; a system control module located in the housing; a main interface on the housing, the main interface includes a plurality of main electrical connectors operably coupled with the system control module and includes one or more main mechanical connectors; a mechanical system located in the housing and mechanically coupled with the one or more main mechanical connectors.

In one embodiment, the mechanic system can include: a spindle gear coupled with a force cable at one end with the other end of the force cable being coupled with the one of the main mechanical connectors, and wherein activating the spindle gear winds the force cable therearound so as to apply a bias to the main mechanical connector; a drive gear engaged with the spindle gear; a mechanical activating member coupled with the drive gear such that activation of the mechanical activating member actuates the drive gear; and a bias system coupled with the drive gear such that the bias system applies a bias to the drive gear.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, hand-held computing systems, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 6:
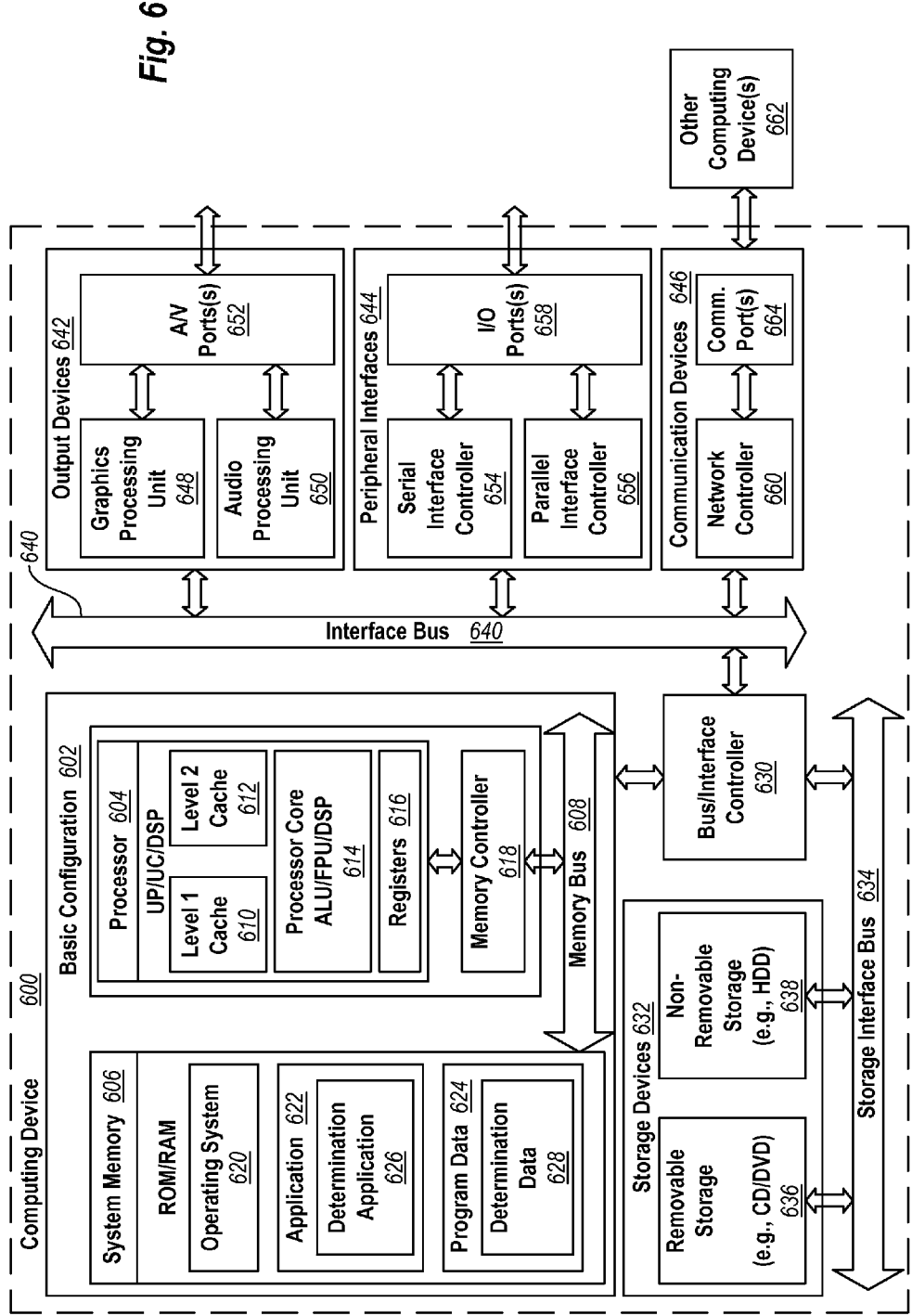
FIG. 6 includes a schematic representation of a computing system that can be used with or included in the base unit of the imaging system, arranged in accordance with at least one of the embodiments described herein, and which arrangement may be modified in accordance with the disclosure provided herein by one of ordinary skill in the art.

FIG. 6 shows an example computing device 600 that is arranged to perform any of the computing methods for imaging. That is, the computing device 600 can be included to operate components of the invention, such as the imaging modules, light sources, as well as any display screen or the like. The computing device 600 can be used to provide instruction data and to receive and analyze image data. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (μP), a microcontroller (μC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on operating system 620 such that the work performed by untrusted computing nodes can be verified as described herein. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. An imaging system comprising:
    a base unit comprising:
        a housing;
        a system control module located in the housing;
        a main interface on the housing, the main interface includes a plurality of main electrical connectors operably coupled with the system control module and includes one or more main mechanical connectors;
        a mechanical system located in the housing and mechanically coupled with the one or more main mechanical connectors; and
        a mechanical activating member mechanically coupled with the mechanical system; and
    one or more imaging units each being configured to be removably coupled to the base unit, the imaging unit comprising:
        an elongate support member having a proximal end, a proximal section, a bendable section, and a distal end;
        an imaging interface on the proximal end of the elongate support member, the imaging interface includes a plurality of imaging electrical connectors that correspond and connect with the main electrical connectors of the main interface and includes one or more imaging mechanical connectors that correspond and connect with main mechanical connectors of the main interface;
        one or more mechanical actuators each having a proximal end mechanically coupled with the one or more imaging mechanical connectors and extending from the imaging interface along the elongate support member to a distal region of the bendable section which is coupled to a distal end of the mechanical actuator; and
        a plurality of electrically conductive elements electronically coupled with the imaging electrical connectors and disposed within the elongate support member and extending from the imaging interface to an imaging module located in the distal end of the elongate support member, wherein one of the main mechanical connectors of the base unit or the imaging mechanical connectors is a female force transfer member having a recess and the other is a male force transfer member with a shaft that slidably fits into the recess of the female force transfer member, wherein one of the female force transfer member or male force transfer member is electromagnetic.

2. The imaging system of claim 1, wherein the main mechanical connectors and imaging mechanical connectors are configured as force transfer connectors when coupled that are configured to transfer mechanical forces from the mechanical system of the base unit to the one or more mechanical actuators in order to bend the bendable section of the elongate support member upon electronic activation.

3. The imaging system of claim 2, wherein the housing includes a power source that is operably coupled with one or more of the plurality of main electrical connectors, which are configured to transfer electrical power from the base unit to the imaging unit.

4. The imaging system of claim 1, wherein the female force transfer member is electromagnetic.

5. The imaging system of claim 4, wherein the male force transfer member is ferromagnetic.

6. The imaging system of claim 1, wherein the housing of the base unit includes one or more main engagement members associated with the main interface and the elongate support member of the imaging unit includes one or more imaging engagement members that are configured to be coupled with the one or more main engagement members when the base unit is coupled to the imaging unit.

7. The imaging system of claim 6, wherein one of the main engagement members or imaging engagement members include an extension with a recess and the other has a protrusion received into the recess of the extension when the base unit is coupled with the imaging unit.

8. The imaging system of claim 1, wherein the bendable section of the elongate support member includes a shape memory member extending from a proximal end to a distal end of the bendable section.

9. The imaging system of claim 1, wherein the shape memory member includes a shape memory alloy that is straight when in its relaxed state.

10. The imaging system of claim 1, wherein the mechanical system includes a spindle gear coupled with a force cable at one end with the other end of the force cable being coupled with the one of the main mechanical connectors, and wherein activating the spindle gear winds the force cable therearound so as to apply a bias to the main mechanical connector.

11. The imaging system of claim 10, wherein the mechanical system includes a drive gear engaged with the spindle gear and a mechanical activating member is coupled with the drive gear such that activation of the mechanical activating member actuates the drive gear.

12. The imaging system of claim 11, wherein the mechanical system includes a bias system coupled with the drive gear such that the bias system applies a bias to the drive gear.

13. A disposable imaging unit comprising:
an elongate support member having a proximal end, a proximal section, a bendable section, and a distal end;
an imaging interface located on the proximal end of the elongate support member, the imaging interface includes a plurality of imaging electrical connectors that correspond and connect with main electrical connectors of a main interface of a base unit, and the imaging interface includes one or more imaging mechanical connectors that correspond and connect with the main mechanical connectors of the main interface of the base unit;
one or more mechanical actuators each having a proximal end mechanically coupled with the one or more imaging mechanical connectors and extending from the imaging interface along the elongate support member to a distal region of the bendable section which is coupled to a distal end of the mechanical actuator; and
a plurality of electrically conductive elements electronically coupled with the imaging electrical connectors and disposed within the elongate support member and extending from the imaging interface to an imaging module located in the distal end of the elongate support member,
wherein one of the main mechanical connectors of the base unit or the imaging mechanical connectors is a female force transfer member having a recess and the other is a male force transfer member with a shaft that slidably fits into the recess of the female force transfer member, wherein one of the female force transfer member or male force transfer member is electromagnetic.

14. The imaging unit of claim 13, wherein the imaging mechanical connectors are coupled to corresponding to the main mechanical connectors of the base unit to form magnetic force transfer connectors, and which are configured to transfer mechanical forces from the base unit to the one or more mechanical actuators in order to bend the bendable section of the elongate support member upon electronic activation.

15. The imaging unit of claim 14, wherein the female force transfer member is an electromagnet.

16. The imaging unit of claim 13, wherein the imaging interface includes one or more imaging engagement members on the elongate support member that are configured to be coupled with one or more main engagement members on the housing when the base unit is coupled to the imaging unit.

17. The imaging unit of claim 13, wherein the bendable section of the elongate support member includes a shape memory member extending from a proximal end to a distal end of the bendable section.

18. The imaging system of claim 13, wherein the shape memory member includes a shape memory alloy that is straight when in its relaxed state.

19. A base unit comprising:
a housing configured to couple with an elongate support member of an imaging unit that couples with the base unit;
a system control module located in the housing;
a main interface on the housing, the main interface includes a plurality of main electrical connectors operably coupled with the system control module and includes one or more main mechanical connectors, wherein the main mechanical connectors are configured to couple with imaging mechanical connectors of the imaging unit;
a mechanical system located in the housing and mechanically coupled with the one or more main mechanical connectors, the mechanical system comprising:
a spindle gear coupled with a force cable at one end with the other end of the force cable being coupled with the one of the main mechanical connectors, and wherein activating the spindle gear winds the force cable therearound so as to apply a bias to the main mechanical connector;
a drive gear engaged with the spindle gear;
a mechanical activating member coupled with the drive gear such that activation of the mechanical activating member actuates the drive gear; and
a bias system coupled with the drive gear such that the bias system applies a bias to the drive gear,
wherein one of the main mechanical connectors of the base unit or the imaging mechanical connectors is a female force transfer member having a recess and the other is a male force transfer member with a shaft that slidably fits into the recess of the female force transfer member, wherein one of the female force transfer member or male force transfer member is electromagnetic and the female force transfer member and male force transfer member slide relative to each other upon electronic activation of the electromagnet.

* * * * *